United States Patent [19]
Engbers

[11] Patent Number: 6,150,472
[45] Date of Patent: Nov. 21, 2000

[54] MULTI-FUNCTIONAL SITE CONTAINING POLYMERS, AND APPLICATIONS THEREOF

[75] Inventor: Gerardus Henricus Maria Engbers, Oldenzaal, Netherlands

[73] Assignee: Holland Biomaterials Group B.V., Netherlands

[21] Appl. No.: 09/152,637

[22] Filed: Sep. 14, 1998

Related U.S. Application Data

[63] Continuation-in-part of application No. 08/769,612, Dec. 18, 1996, abandoned.

[30] Foreign Application Priority Data

Dec. 22, 1995 [EP] European Pat. Off. .............. 95203602

[51] Int. Cl.⁷ .............................. C08G 63/48; C08G 63/91
[52] U.S. Cl. .................. 525/404; 525/54.21; 525/54.23; 525/54.24; 525/54.26; 525/54.3; 525/54.31; 435/177; 435/180; 435/182; 530/812; 530/815; 530/817
[58] Field of Search ................................ 525/54.2, 54.21, 525/54.23, 54.24, 54.26, 54.3, 54.31; 435/177, 180, 182; 530/812, 815, 817

[56] References Cited

U.S. PATENT DOCUMENTS 3,616,935  11/1971  Love et al. .
3,993,553  11/1976  Assarsson et al. ........................ 522/88
5,132,108   7/1992  Narayanan et al. .
5,165,919  11/1992  Sasaki et al. .
5,834,556  11/1998  Desai et al. ............................ 525/54.1

FOREIGN PATENT DOCUMENTS 0294905  8/1988  European Pat. Off. .
9220349  11/1992  WIPO .

OTHER PUBLICATIONS

"Hydrogels Préparés par le Greffage Radiochimique pour l'Immobilisation des Enzymes," Journal of Polymer Science, Polymer Chemistry Edition, vol. 21, No. 8, 1983, New York US, pp. 2589–2596.

*Primary Examiner*—Nathan M. Nutter
*Attorney, Agent, or Firm*—Webb Ziesenheim Logsdon Orkin & Hanson, P.C.

[57] ABSTRACT

Polymers having multi-functional sites and a gel comprising a solvent swollen network of cross-linked polymer(s), of which at least one polymer comprises at least one multi-functional site. A multi-functional site is a sequence of more than one functional group. A multi-functional polymer is a polymer comprising one or more multi-functional sites and/or more than one functional group.

8 Claims, No Drawings

MULTI-FUNCTIONAL SITE CONTAINING POLYMERS, AND APPLICATIONS THEREOF

This is a continuation-in-part of U.S. application Ser. No. 08/769,612, filed Dec. 18, 1996, now abandoned.

The present invention relates to multi-functional site containing polymers and applications thereof, in particular gels.

Gels have a wide variety of applications, for instance in the biomedical field as coatings, in contact lenses and in drug delivery systems but also in the non medical field such as coatings and cosmetic applications.

A hydrogel has been defined (Peppas et al., Hydrogels in Medicine and Pharmacy, Vol.I fundamentals, Chapter I, pages 1–25, (1986) CRC Press Inc. Boca Raton, USA) as a water swollen network (cross-linked structure) of hydrophilic homo-polymers or copolymers with a three dimensional appearance of which the cross-links can be formed by covalent and/or ionic bonds, and/or by van der Waals and/or hydrogen bonds.

Analogously a gel can be defined as such a network of homo-polymers or copolymers which is swollen by means of a solvent or a mixture of solvents.

In general one can presently discern two different methods of gel preparation: cross-linking of a homo-polymer or copolymer with functional groups along the polymer chain (pendant groups) and subsequent swelling in an appropriate solvent (for hydrogels water or aqueous solutions), or simultaneous polymerisation and cross-linking of one or more mono-functional and one multi-functional monomer followed by swelling in an appropriate solvent or mixture of solvents.

An example of the first method of gel preparation is the cross-linking of polyvinyl alcohol by a mixture of aldehydes. Typical monomers that are used in the latter approach are methacrylates like hydroxyethyl methacrylate (mono-functional) and ethylene glycol dimethacrylate (bi-functional/multi-functional). Characteristics of the obtained gel are determined by the choice of polymer/monomer(s) used for its preparation, the degree and positioning of cross-linking and the solvent used for swelling of the network.

Making use of these known methods the preparation of currently available gels is accompanied by the occurrence of one or more of the following phenomena:

i) cross-linking of the polymer chains within the swollen network occurs randomly along the polymer chains; and ii) the constituents are not quantitatively incorporated in the resulting polymer network (see also example 1); and iii) each cross-linker molecule does not yield a cross-link.

Cross-linking occurring randomly along the polymer chain causes that a polymer network is obtained with a non-uniform length between cross-links. Monomer/polymer not being completely build in in the polymer network causes that the composition and/or the cross-link density of the final network is hard to pre-define and/or that gel components are released during application. Cross-linker not being completely used causes that the cross-link density is only proportional to the theoretical cross-link ratio (moles cross-linking agent divided by moles of polymer repeating units), whereby prediction of the number of cross-links on the basis of the cross-link ratio is hindered.

This results in gels of which the chemical, mechanical and physical characteristics are difficult to pre-determine and which can only be reproducibly prepared when all conditions are kept within narrow margins. This makes these conventional methods of gel-preparation less suitable for the preparation of 'tailor made' gels having specific qualities for desired uses.

An object of the present invention is to provide multi-functional site containing polymers and applications thereof in improved gels.

According to a first aspect the present invention provides polymers with multi-functional sites. According to a second aspect the present invention provides a gel comprising a solvent swollen network of cross-linked polymer(s), of which at least one polymer comprises at least one multi-functional site.

For the present invention the following definitions are used: a functional group is a chemical entity which is capable to directly or indirectly (via a reagent) participate in a reaction or interaction, for instance cross-linking.

A multi-functional site is a sequence of more than one functional group.

A multi-functional polymer is a polymer comprising one or more multi-functional sites and/or more than one functional group.

An end-multi-functional polymer is a polymer (including star-like polymers) having at least at one end of the polymer chain a multi-functional site. In one embodiment the multi-functional sites are at both or at all ends of the polymer.

A core-multi-functional polymer is a polymer having as a core a multi-functional site and grafted/bound thereto at least one polymer chain resulting in more than one polymer end-group. Within one polymer more than one core may be present.

A pendant-multi-functional polymer is a polymer having along the polymer chain as a side group more than one functional group.

A homo-multi-functional polymer is a polymer with only one type of functional group whereas a hetero-multi-functional polymer is a polymer with more than one type of functional group.

By utilising polymers with multi-functional sites, as described above, the inventors have developed gels with regular network structures and/or a better incorporation of the polymers in the final network.

Advantages of the use of polymers with multi-functional units over the use of polymers with mono-functional units for the preparation of polymeric networks are:

i) enhanced reactivity; the statistical chance of coupling with multi-functional units is increased. This results in shorter reaction and gelation times (see also example 2) and a large degree of freedom in reaction conditions and in a better incorporation of gel components in the network; and ii) enhanced stability of the resulting network preventing or retarding the release of network components (see also example 2). Possibly this arises from multi-point attachment per functional site.

These two advantages result in a better control over the gel properties (chemical, physical and mechanical) enabling to control important gel-parameters like the cross-link density, permeability, swelling and mechanical strength.

Additionally, with the multi-functional sites an additional phase is incorporated in the gel that may retain functionality. This can for instance be used for the immobilisation (chemically or physically) of additional components that need to be released (drugs) or taken up (toxic substances) or to influence the swelling of the gel. This phase can also be functional in the adhesion/immobilisation of the gel to a substrate.

Further, an enlarged flexibility in network compositions can be covered (see also example 3). The use of end-multi-functional polymers offers the possibility to obtain mechanically stable networks with very high swelling characteristics.

In the case the functional sites are positioned at the ends of a polymer chain this type of polymer has an absence of cross-link sites between the chain ends, providing control over the degree and positioning of cross-links within the gel network.

By choosing a specific polymer chain length between the multi-functional sites, the swelling characteristics and the distance between two cross-links of the desired gel can be controlled.

Hence according to the present invention, control over the degree and positioning of cross-linking is achieved, whereby a gel with a pre-determined network structure is yielded whereby control over the gel's characteristics, such as permeability, swelling and strength, is achieved.

An improved process for making a gel, according to the invention, comprises of adding at least one multi-functional site containing polymer to a solvent (or mixture of solvents) and wherein, on gel formation, functional units of different polymer molecules are coupled whereby such coupling can be continued to build up a network of cross-linked chains, whereby said network includes the solvent (or mixture of solvents) thus forming a gel.

Another improved process for making a gel, according to the invention, comprises of adding one or more homo-end-multi-functional polymer(s) to a solvent (or a mixture of solvents) and wherein, on gel formation, end-multi-functional groups of different molecules are coupled whereby such coupling can be continued to build up a network of cross-linked chains, whereby said network includes the solvent (or the mixture of solvents) thus forming the gel.

Another improved process for making gels, according to the invention, comprises of mixing together one or more different homo-end-multi-functional polymer(s) and/or one or more hetero-end-multi-functional polymer(s) and a solvent (or a mixture of solvents), wherein, on gel formation, end-functional groups couple whereby such coupling can be continued between further chains until a network of cross-linked chains builds up, said network including the solvent (or the mixture of solvents) to form a gel.

A fourth improved process for making gels, according to the invention, comprises of mixing together one or more homo-end-multi-functional polymer(s) and/or one or more hetero-end-multi-functional polymer(s) with one or more homo-pendant-multi-functional polymer(s) and/or one or more hetero-pendant-multi-functional polymer(s) and a solvent (or a mixture of solvents) wherein, on gel formation, end-functional groups couple with end-functional groups and/or with pendant-functional groups, whereby such coupling can be continued between further chains until a network of cross-linked chains builds up, said network including the solvent (or the mixture of solvents) to form a gel.

An additional improved process for making gels, according to the invention, comprises of mixing together one or more homo-core-multi-functional polymer(s) and one or more homo-pendant-multi-functional polymer(s) and/or one or more hetero-pendant-multi-functional polymer(s) and a solvent (or a mixture of solvents) wherein, on gel formation, core-functional groups couple with pendant-functional groups, whereby such coupling can be continued between further chains until a network of cross-linked chains builds up, said network including the solvent (or the mixture of solvents) to form a gel.

For coupling of one type of homo-multi-functional polymers the use of a cross-linker or catalyst is required. When using hetero-multi-functional polymers (if desired) in combination with homo-multi-functional polymers the use of a cross-linker is preferred. The cross-linker may be an organic molecule, multivalent ions and an energy source like for instance light, ultraviolet or gamma-radiation. For the cross-linking of aqueous systems containing both carboxylic acid and amine functional groups a preferred cross-linker for the preparation of hydrogels is N-ethyl-N'-(3-dimethylaminopropyl)-carbodiimide. In the case cross-linking leads to the formation of biodegradable bonds, biodegradable gels are obtained.

According to the present invention the chemical nature of the chains and the chemical nature of the multi-functional groups/coupling groups can be different, for example these being non-ionic, anionic or cationic.

By pre-selecting the chain lengths and type of solvent, and the chemical nature of the chains and multi-functional site(s), gels can be produced with a combination of desired characteristics.

The multi-functional site is preferably selected from the group oligomers or polymers based on: acrylates, acrylic acid, allylamines, amino-acids, sugars/saccharides, dendrimers, ethylene imine, vinylalcohol, styrene, azido-compounds, etc., and derivatives thereof like for instance cellulose, dextran, chitosan, chitine, etc..

In the case of end-multi-functional polymers that substantially lack functional groups between the chain ends, and wherein the chemical nature of the multi-functional groups is substantially the same (homo-end-multi-functional polymers), the polymer is preferably selected from the group consisting of: poly(ethylene imine)-poly(ethylene oxide)-poly(ethylene imine) triblock copolymer, poly(acrylic acid)-poly(ethylene oxide)-poly(acrylic acid) triblock copolymer, poly(ethylene imine)-poly(ethylene oxide-co-propylene oxide)-poly(ethylene imine) triblock copolymer, poly (acrylic acid)-poly(ethylene oxide-co-propylene oxide)-poly (acrylic acid) triblock copolymer, poly(ethylene imine)-poly (ethylene oxide)-poly(propylene oxide)-poly(ethylene oxide)-poly(ethylene imine) pentablock copolymer, poly (ethylene imine)-poly (propylene oxide)-poly (ethylene oxide)-poly(propylene oxide)-poly(ethylene imine) pentablock copolymer, poly(acrylic acid)-poly(ethylene oxide)-poly(propylene oxide)-poly(ethylene oxide)-poly(acrylic acid) pentablock copolymer, poly(acrylic acid)-poly (propylene oxide)-poly(ethylene oxide)-poly(propylene oxide)-poly(acrylic acid) pentablock copolymer, In the case of core-multi-functional polymers, the polymer is preferably selected from the group consisting of: poly(ethylene oxide)$_n$-poly(ethylene imine), poly(ethylene oxide)$_n$-poly(acrylic acid), poly(ethylene oxide)-poly (propylene oxide)copolymer$_n$-poly(ethylene imine), poly (ethylene oxide)-poly(propylene oxide)copolymer$_n$-poly (acrylic acid), In the case of pendant multi-functional polymers, the polymer is preferably selected from the group consisting of pendant multi-functional homo- and copolymers: carboxymethyl cellulose, carboxymethyl dextran, carboxymethyl amylose, chitine, chitosan, chondriotine sulphate, dendrimers, dextran sulphate, heparan sulphate, heparin, poly(acrylic acid), poly(methacrylic acid), poly(amino acids) including copolymers, poly(ethylene imine), poly (hydroxyethyl methacrylate-methacrylic acid), polysaccharides, proteins, Examples of anionic functional groups include $COO^-$, $SO_3^-$, $SO_4^-$, $PO_4^{2-}$, etc., examples of cationic functional groups include $N^+RR'R''$, $N^+R_2R'$, $N^+R_3$, $N^+R_2H$, $N^+RR'H$, $N^+H_3$, etc. and examples of non-ionic functional groups include aldehyde, amino, carboxy, epoxy, halogen, hydroxyl, thiol, etc.

It should be noted that certain functional groups have been accorded the non-ionic and ionic status, for instance the carboxylic acid group and amino group. The reason for this is that these groups are used for covalent binding in some applications and in other applications for ionogenic interaction. In the first instance these groups are considered to be non-ionic and in the second instance ionic.

Further aspects of the invention include applications of the gels and uses thereof. For example as an anti-thrombogenic lubricious coating of a medical article or system (see example 6).

The invention relates further to multi-functional site containing polymers like triblock, pentablock and star-like copolymers as such.

The synthesis of end-multi-functional triblock and pentablock copolymers can be performed as follows:

carbonyldiimidazole activated poly(ethylene oxide) (alpha,omega di-oxycarbonylimidazole poly(ethylene oxide)) is added to an aqueous solution containing a molar excess of poly(ethylene imine) of pH 8. After overnight reaction at room temperature non-reacted poly(ethylene imine) is removed by ultra-filtration and the tri-block copolymer is isolated by freeze drying. Analogous pentablock copolymers can be synthesised by using alpha, omega di-oxycarbonylimidazole poly(ethylene oxide)-poly(propylene oxide)-poly(ethylene oxide) or alpha, omega di-oxycarbonylimidazole poly(propylene oxide)-poly(ethylene oxide)-poly(propylene oxide) triblock copolymers in stead of alpha,omega di-oxycarbonylimidazole poly(ethylene oxide).

Poly(acrylic acid) is activated with N-ethyl-N'-(3-dimethylaminopropyl)-carbodiimide and added to an aqueous solution containing a molar short measure of alpha, omega-di-amino poly(ethylene oxide) of pH 8. After overnight reaction at room temperature non-reacted poly(acrylic acid) is removed by ultra-filtration and the triblock copolymer is isolated by freeze drying. Analogous pentablock copolymers can be synthesised by using alpha, omega di-amino poly(ethylene oxide)-poly(propylene oxide)-poly(ethylene oxide) or alpha, omega-di-amino poly(propylene oxide)-poly(ethylene oxide)-poly(propylene oxide) triblock copolymers in stead of alpha,omega di-amino poly(ethylene oxide).

Methods for the conversion of polymer hydroxyl end-groups to amino end-groups as well as for the activation of hydroxyl groups by carbonyldiimidazole are extensively described in literature.

An example of the synthesis of a hetero-multi-functional polymer is as follows: heparin fragments that are obtained by nitrous acid degradation of heparin are activated by N-ethyl-N'-(3-dimethylaminopropyl)-carbodiimide and subsequently added to an aqueous solution containing a molar short measure of alpha,omega di-amino poly(ethylene oxide) of pH 8. After overnight reaction at room temperature non-reacted heparin fragments are removed by ultra-filtration and the triblock copolymer is isolated by freeze drying.

Analogous pentablock copolymers can be synthesised by using alpha,omega di-amino poly(ethylene oxide)-poly(propylene oxide)-poly(ethylene oxide) or alpha, omega di-amino poly(propylene oxide)-poly(ethylene oxide)-poly(propylene oxide) triblock copolymers in stead of alpha, omega di-amino poly(ethylene oxide).

An example of the synthesis of core-multi-functional polymers (star-like copolymers) is as follows: carbonyldiimidazole activated mono-methoxy poly(ethylene oxide) is added to poly(ethylene imine) in an aqueous solution of pH 8. After overnight reaction at room temperature non-reacted poly(ethylene oxide) was removed by ultra-filtration and the star-like copolymer was isolated by freeze drying.

Analogously alpha-amino, omega-methoxy poly(ethylene oxide) was added to N-ethyl-N'-(3-dimethylaminopropyl)-carbodiimide activated poly(acrylic acid) of pH 8. After overnight reaction at room temperature non-reacted poly(ethylene oxide) was removed by ultra-filtration and the star-like copolymer was isolated by freeze drying.

The invention will now be further described by way of the following specific examples.

EXAMPLE 1 alpha,omega-Diamino polyethylene(oxide) (30 mg) with a molecular weight of 10.000, sodium heparin (24 mg) and N-hydroxysuccinimide (2 mg) were dissolved in 1.25 ml of water and the pH of the solution was adjusted to 6.6. A solution of N-ethyl-N'-(3-dimethylaminopropyl)-carbodiimide hydrochloride in water (100 $\mu$l, 200 mg/ml) was added. The resulting gel was extracted 3 times for 24 hrs with phosphate buffered saline after which the gel was reacted with a potassium tetraborate buffered solution of trinitrobenzene sulphonic acid. During this reaction the gel coloured yellow, indicating the presence of free, non-reacted amino groups meaning that the poly(ethylene oxide) has not fully participated in the cross-linking of the network.

EXAMPLE 2

Two analogous gels based on poly(ethylene oxide) (PEO) or on poly(ethylene imine)-poly(ethylene oxide)-poly(ethylene imine) tri-block copolymer (PEI-PEO-PEI) were prepared. The molecular weight of the poly(ethylene oxide) was 10.000 whereas the molecular weight of the triblock copolymer was 11.200 in which the polyethylene oxide block of molecular weight of 10.000 was end-capped with two poly(ethylene imine) blocks of molecular weight 600.

alpha,omega-Diamino polyethylene(oxide) (273 mg), sodium heparin (225 mg) and N-hydroxysuccinimide (18 mg) were dissolved in 11.25 ml of water and the pH of the solution was adjusted to 6.6. After vacuum degassing the solution was divided over 9 vials with each 1,25 ml.

Poly(ethylene imine)-poly(ethylene oxide)-poly(ethylene imine) tri-block copolymer (305 mg), sodium heparin (225 mg) and N-hydroxysuccinimide (18 mg) were dissolved in 11.25 ml of water and the pH of the solution was adjusted to 6.6. After vacuum degassing the solution was divided over 9 vials with each 1,25 ml.

A solution of N-ethyl-N'-(3-dimethylaminopropyl)-carbodiimide hydrochloride in water (400 mg in 2 ml) was prepared and to all vials 100 $\mu$l of this solution was added. The vials were incubated at room temperature for 21,5 hrs after which the gels were after-cured at 50° C. for another 8,5 hrs. The time of gelation was determined. The gels were extracted with phosphate buffered saline three times each 24 hrs and the amount of heparin that was incorporated in the gel was calculated from the starting amount of heparin and the amount of heparin that was extracted from the gels. The extracted amount of heparin in the extraction solutions was determined with an Azure-A assay. The results for the two types of gels are presented below:

| gel type | gelation time | gel appearance | incorporated heparin |
|---|---|---|---|
| PEO | ±8.5 hrs. | mechanically weak | 91.6 ± 0.8% |
| PEI-PEO-PEI | ±35 min. | mechanically strong | 102.4 ± 2.0% |

EXAMPLE 3 alpha,omega-Diamino polyethylene(oxide) (236 mg, molecular weight 10.000), sodium heparin (250 mg) and N-hydroxysuccinimide (20 mg) were dissolved in 20.2 ml of water and the pH of the solution was adjusted to 7.

Poly(ethylene imine)-poly(ethylene oxide)-poly(ethylene imine) tri-block copolymer (265 mg, molecular weight 600 and 10.000 for the poly(ethylene imine) and poly(ethylene oxide) blocks, respectively), sodium heparin (250 mg) and N-hydroxysuccinimide (20 mg) were dissolved in 20.2 ml of water and the pH of the solution was adjusted to 7.0.

To both solutions a solution of N-ethyl-N'-(3-dimethylaminopropyl)-carbodiimide hydrochloride (200 mg/ml, 2 ml) was added. The tri-block copolymer solution gelled after ±3,5 hrs whereas the poly(ethylene oxide) based solution did not form a gel within a week.

EXAMPLE 4

Poly(ethylene imine)-poly(ethylene oxide)-poly (propylene oxide)-poly(ethylene oxide) poly(ethylene imine) penta-block copolymer (500 mg) with a molecular weight of the poly(ethylene imine), poly(ethylene oxide) and poly(propylene oxide) blocks of 600, 4200 and 3600 respectively was dissolved in 2,5 ml of water. Poly(acrylic acid) sodium salt (65 mg) and N-hydroxysuccinimide (7 mg) were dissolved in 750 µl of water and added to the penta-block containing solution. The pH of the solution was adjusted to 7,5 after which the solution was vacuum degassed. Subsequently 2 ml of a suspension of *Nitrosomonas europaea* were added and the solution was cooled to 4° C. A solution of N-ethyl-N'-(3-dimethylaminopropyl)-carbodiimide hydrochloride in water (78 mg in 250 µl) was added to the cell suspension and gelled over night at 4° C. resulting in a stable gel.

EXAMPLE 5

Poly(ethylene imine)-poly(ethylene oxide)-poly(ethylene imine) triblock copolymer (50 mg), heparin sodium salt (25 mg) and N-hydroxysuccinimide (1 mg) were dissolved in 1.75 ml water whereafter 9 mg N-ethyl-N'-(3-dimethylaminopropyl)-carbodiimide hydrochloride were added. Within 20 minutes a gel was obtained.

EXAMPLE 6

Poly(ethylene imine)-poly(ethylene oxide)-poly(ethylene imine) triblock copolymer (100 mg), heparin sodium salt (50 mg) and N-hydroxysuccinimide (2 mg) were dissolved in 3.5 ml water and the solution was degassed by vacuum suction. Subsequently 18 mg N-ethyl-N'-(3-dimethylaminopropyl)-carbodiimide hydrochloride were added. This solution was used to coat the inside of poly (ethylene) tubes. After curing and extensive rinsing with water and phosphate buffered saline the tubes were filled with 1.5 ml citrated whole human blood after which 200 µl 0.1 M $CaCl_2$ in 0.9% saline was added. The tubes were closed and rotated and the time until clotting was determined. For the hydrogel coated tubes (n=4) clotting did not occur within 3.5 hours whereas for non-coated control tubes (n=4) the clotting time was 24±1 minutes.

EXAMPLE 7

Carboxymethyl dextran (25 mg) and poly(ethylene imine)-poly(ethylene oxide)-poly(ethylene imine) triblock copolymer (50 mg) were dissolved in 8 ml water yielding a solution of pH 6.5–7.0. After the addition of 200 µl N-ethyl-N'-(3-dimethylaminopropyl)-carbodiimide hydrochloride (10 mg/ml) gelation occurred within 1 hr.

EXAMPLE 8

Poly(acrylic acid) (0.46 gram of a 25 w % solution in water) was diluted with 6.55 ml water and the pH of the solution was adjusted to 5.2. whereafter 2 ml of a 25 mg/ml N-ethyl-N'-(3-dimethylaminopropyl)-carbodiimide hydrochloride solution in water was added. After the addition of poly(ethylene imine)-poly(ethylene oxide)-poly(ethylene imine) triblock copolymer (47.2 mg) that was dissolved in 2 ml water instantaneous gelation occurred.

EXAMPLE 9

Poly(ethylene imine)-poly(ethylene oxide)-poly(ethylene imine) triblock copolymer (50 mg), heparin sodium salt (25 mg) and N-hydroxysuccinimide (2 mg) were dissolved in 2 ml water after which 0,67 ml dimethylsulfoxide was added resulting in a solution of pH 6.0–6.5. N-Ethyl-N'-(3-dimethylaminopropyl)-carbodiimide hydrochloride (10 mg in 100 µl water) was added to the solution and within 1.5 hrs reaction at room temperature gelation was observed.

EXAMPLE 11

N-hydroxysuccinimide (HNS, 20 mg) was added to 18 ml of a carboxymethyl cellulose (CMC) solution in phosphate buffered saline (PBS, 5 mg CMC/ml). After complete dissolution of the NHS, N-ethyl-N'-(3-dimethylaminopropyl)-carbodimide (EDC, 70 mg) was added and the solution as mixed for 5 minutes to allow activation of carboxylic acid groups.

In the mean time, 2 ml of a solution of poly(ethylene imine)-poly(ethylene oxide)-poly(ethylene imine) triblock copolymer with a molecular weight of 21.200 D (molecular weight of poly(ethylene imine) blocks 600 D) in PBS (100 mg triblock copolymer/ml PBS) was mixed with 1.72 ml of a yeast suspension and the resulting suspension was subsequently added to the activated CMC solution while mixing. Directly after this addition the complete yeast suspension was poured into a stirred, baffled reaction vessel which contained 200 ml hexadecane. After gelation, these spheres containing the immobilized yeast were isolated by sieving and rinsed with a solution of glucose in PBS (10 gram/liter).

EXAMPLE 10

Carboxymethyl cellulose sodium salt (50 mg, high viscosity grade) was dissolved in 3 ml 3 M NaCl in water and the pH of the solution was adjusted to 7.5–8.0. From a star-like copolymer, consisting for 58 m % of poly(ethylene imine) with a molecular weight of 50.000 and the remaining 42 m % of poly(ethylene oxide) of a molecular weight of 5.000, 20 mg, dissolved in 2.5 ml 3 M NaCl in water was added and the pH of the solution was again adjusted to 7.5–8.0. N-Ethyl-N'-(3-dimethylaminopropyl)-carbodiimide hydrochloride (70 mg in 0.5 ml water) was added and gelation was observed within 5.5 hours reaction at room temperature.

By making gels according to the processes of the present invention, the inventors have been able to improve the degree and positioning of cross-linking in the network, thereby yielding the possibility to design accurately 'tailor-made' gels with specific properties for specific applications. For example, a gel is formed by the combination of alpha, omega homo-end-multi-functional poly(ethylene oxide) and a hetero-pendant-multi-functional polymeric anticoagulant like heparin, which, when applied as a coating gives a slippery, antithrombogenic surface. By proper selection of the polymers a gel with tailor-made bulk and/or surface properties can be obtained.

Other conceivable applications of gels according to the present invention include bone-bonding surfaces, non-fouling surfaces, drug release systems, micro-spheres, detoxification systems, immobilisation systems for cells, enzymes or micro-organisms, intra-ocular and contact lenses, vascular system 'repair' material, tissue matrices, anti-bacterial coatings, and water binding systems.

What is claimed is:

1. A polymer network comprising a block copolymer crosslinked to a polysaccharide, said block copolymer essentially comprising at least two different polymer blocks selected from poly(ethylene imine), poly(ethylene oxide), poly(propylene oxide) and poly(acrylic acid), said polysaccharide being selected from the group consisting of carboxymethyl cellulose, carboxymethyl dextran, carboxymethyl amylose, chitin, chitosan, chondroitin, dextran sulfate, heparin and heparin sulfate.

2. A polymer network as claimed in claim 1, wherein the polysaccharide is one of heparin and heparin sulfate.

3. A polymer network as claimed in claim 2, wherein the polymer is a triblock polymer of poly(ethylene imine)-poly(ethylene oxide)-poly(ethylene imine).

4. A polymer network as claimed in claim 1, wherein the polysaccharide is carboxymethyl cellulose and the copolymer consists of a poly(ethylene imine) core with a plurality of poly(ethylene oxide) chains grafted thereto.

5. A polymer network as claimed in claim 4, wherein the polymer is a pentablock polymer of poly(ethylene imine)-poly(ethylene oxide)-poly(propylene oxide)-poly(ethylene oxide)-poly(ethylene imine).

6. A polymer network comprising a triblock polymer of poly(ethylene imine)-poly(ethylene oxide)-poly(ethylene imine) crosslinked to a polysaccharide selected from the group consisting of carboxymethyl cellulose, carboxymethyl dextran, carboxylmethyl amylose, chitin, chitosan, chondroitin, dextran sulfate, heparin and heparin sulfate.

7. A polymer network as claimed in claim 6, wherein the poly(ethylene oxide) block has a molecular weight of about 10,000 and is capped at each end with a poly(ethylene imine) block having a molecular weight of about 600.

8. A polymer network comprising a pentablock polymer of poly(ethylene imine)-poly(ethylene oxide)-poly(propylene oxide)-poly(ethylene oxide)-poly(ethylene imine) crosslinked to carboxymethyl cellulose.

* * * * *